United States Patent
Larose et al.

(10) Patent No.: US 10,525,179 B2
(45) Date of Patent: Jan. 7, 2020

(54) CRENELLATED INFLOW CANNULA

(71) Applicant: HeartWare, Inc., Miami Lakes, FL (US)

(72) Inventors: Jeffrey A. Larose, Sunrise, FL (US); Charles R. Shambaugh, Coral Gables, FL (US); Mustafa E. Taskin, Cooper City, FL (US)

(73) Assignee: HeartWare, Inc., Miami Lakes, FL (US)

( * ) Notice: Subject to any disclaimer, the term of this patent is extended or adjusted under 35 U.S.C. 154(b) by 189 days.

(21) Appl. No.: 15/472,669

(22) Filed: Mar. 29, 2017

(65) Prior Publication Data
US 2017/0281841 A1    Oct. 5, 2017

Related U.S. Application Data

(60) Provisional application No. 62/315,758, filed on Mar. 31, 2016.

(51) Int. Cl.
*A61M 1/12* (2006.01)
*A61M 1/10* (2006.01)

(52) U.S. Cl.
CPC ........ *A61M 1/1036* (2014.02); *A61M 1/1086* (2013.01); *A61M 1/122* (2014.02)

(58) Field of Classification Search
CPC ............................ A61M 1/1036; A61M 1/122
See application file for complete search history.

(56) References Cited

U.S. PATENT DOCUMENTS 5,928,253 A    7/1999    Sherman et al.
5,972,030 A    10/1999   Garrison et al.
(Continued)

FOREIGN PATENT DOCUMENTS

AU    2013273663 A1    1/2014
WO    2008136979 A1    11/2008
(Continued)

OTHER PUBLICATIONS

Berlin Heart GmbH, INCO Superior Pump, Implantable Left Ventricle Assist Device, Version 5000033x04, May 2013, 10 pages.
(Continued)

*Primary Examiner* — William J Levicky
(74) *Attorney, Agent, or Firm* — Christopher & Weisberg, P.A.

(57) ABSTRACT

A blood pump including a housing defining a fluid flow path, an upstream end, a downstream end, and an outlet at the downstream end. A rotor is disposed within the housing and within the fluid flow path, the rotor being rotatable independent of the housing in a first direction and configured to pump blood downstream toward the outlet. The housing defines an inflow cannula at the upstream end, the inflow cannula defining a proximal end proximate the rotor and an opposite distal end. The inflow cannula defines a major longitudinal axis and minor longitudinal axis, the distal end of inflow cannula defines a plurality of slots radially disposed about the distal end, the plurality of slots being at least one from the group consisting of sloped in the first direction with respect to the major longitudinal axis and angled in the first direction with respect to the minor longitudinal axis.

19 Claims, 6 Drawing Sheets

(56) References Cited

U.S. PATENT DOCUMENTS

| | | |
|---|---|---|
| 6,033,420 A | 3/2000 | Hahnen |
| 6,129,713 A | 10/2000 | Mangosong et al. |
| 6,146,400 A | 11/2000 | Hahnen |
| 6,159,178 A | 12/2000 | Sharkawy et al. |
| 6,350,252 B2 | 2/2002 | Ray et al. |
| 6,352,530 B1 | 3/2002 | Mangosong |
| 6,451,054 B1 | 9/2002 | Stevens |
| 6,589,206 B1 | 7/2003 | Sharkawy et al. |
| 6,592,547 B2 | 7/2003 | Grimes et al. |
| 6,645,193 B2 | 11/2003 | Mangosong |
| 6,688,861 B2 | 2/2004 | Wampler |
| 6,712,797 B1 | 3/2004 | Southern, Jr. |
| 6,902,556 B2 | 6/2005 | Grimes et al. |
| 6,978,176 B2 | 12/2005 | Lattouf |
| 7,247,162 B1 | 7/2007 | Thornton |
| 7,526,342 B2 | 4/2009 | Chin et al. |
| 7,575,423 B2 | 8/2009 | Wampler |
| 7,686,758 B2 | 3/2010 | Nose et al. |
| 7,976,271 B2 | 7/2011 | LaRose et al. |
| 8,007,254 B2 | 8/2011 | LaRose et al. |
| 8,157,812 B2 | 4/2012 | Barr |
| 8,157,833 B2 | 4/2012 | Au et al. |
| 8,298,185 B2 | 10/2012 | Worrel et al. |
| 8,403,823 B2* | 3/2013 | Yu .................... A61M 1/10 600/16 |
| 8,419,609 B2 | 4/2013 | Shambaugh, Jr. et al. |
| 8,551,112 B2 | 10/2013 | Thornton |
| 8,852,072 B2 | 10/2014 | LaRose et al. |
| 8,951,275 B2 | 2/2015 | Cannon et al. |
| 9,636,441 B2* | 5/2017 | Jarvik .................. A61M 1/10 |
| 2004/0171905 A1 | 9/2004 | Yu et al. |
| 2007/0049787 A1* | 3/2007 | Nose .................... A61M 1/122 600/16 |
| 2008/0021394 A1* | 1/2008 | LaRose ................ A61M 1/101 604/151 |
| 2010/0022939 A1* | 1/2010 | Schima ............... A61M 1/3653 604/6.16 |
| 2015/0223839 A1* | 8/2015 | Spence ............. A61B 17/0218 606/185 |
| 2015/0367048 A1 | 12/2015 | Brown et al. |

FOREIGN PATENT DOCUMENTS

| | | |
|---|---|---|
| WO | 2009058726 A1 | 5/2009 |
| WO | 2010008560 A1 | 1/2010 |
| WO | 2013086147 A2 | 6/2013 |

OTHER PUBLICATIONS

International Search Report and Written Opinion dated Jun. 7, 2017, for corresponding International Application No. PCT/US2017/024693; International Filing Date: Mar. 29, 2017 consisting of 12-pages.

* cited by examiner

CRENELLATED INFLOW CANNULA

CROSS-REFERENCE TO RELATED APPLICATION

This application is related to and claims priority to U.S. Provisional Patent Application Ser. No. 62/315,758, filed Mar. 31, 2016, entitled CRENELLATED INFLOW CANNULA, the entirety of which is incorporated herein by reference.

STATEMENT REGARDING FEDERALLY SPONSORED RESEARCH OR DEVELOPMENT n/a

TECHNICAL FIELD

The present invention relates to implantable blood pumps, and in particular, a blood pump having a crenelated inflow cannula.

BACKGROUND

Blood pumps are commonly used as elements of mechanical circulatory support devices or "MCSDs." MCSDs are normally used to aid the pumping action of a diseased heart. An MCSD that is arranged to aid the pumping action of a ventricle is also referred to as a ventricular assist device or "VAD."

A blood pump used in an MCSD typically is implanted within the patient, with the inlet of the pump communicating with a chamber of the heart, such as a ventricle and with the outlet of the pump connected to an artery. The pump is actuated to draw blood from the ventricle and pump it into the artery. The heart continues to beat, so that some blood may also be passed out of the ventricle through a valve such as the aortic valve. A condition referred to as a "suction" condition can occur when VAD tries to draw more blood than is available. When such a suction condition occurs, the chamber of the heart may collapse, so that a wall of the chamber is drawn toward the pump inlet and blocks the inlet. In extreme cases, such a condition can cause bruising or other injury to heart tissue. Moreover, the chamber wall may remain in place at the pump inlet for some time after the imbalance in flow has been corrected. Accordingly, MCSDs commonly incorporate control circuitry that maintains the flow through the pump at a safe value unlikely to cause a suction condition.

SUMMARY

The present invention advantageously provides a blood pump including a housing defining a fluid flow path. The housing defines an upstream end, a downstream end, and an outlet at the downstream end. A rotor is disposed within the housing and within the fluid flow path, the rotor being rotatable independent of the housing in a first direction and configured to pump blood downstream toward the outlet. The housing defines an inflow cannula at the upstream end, the inflow cannula defining a proximal end proximate the rotor and an opposite distal end. The inflow cannula further defines a major longitudinal axis and minor longitudinal axis, the distal end of inflow cannula defines a plurality of slots radially disposed about the distal end, the plurality of slots being at least one from the group consisting of sloped in the first direction with respect to the major longitudinal axis and angled in the first direction with respect to the minor longitudinal axis.

In another aspect of this embodiment, the housing defines a rotor space, and wherein the rotor is disposed within the rotor space, and wherein the inflow cannula is mounted in fixed spatial relationship with the rotor space.

In another aspect of this embodiment, the rotor defines a plurality of fluid flow slots, and wherein the number of slots in the plurality of fluid flow slots is different than the number of slots in the plurality of slots.

In another aspect of this embodiment, the plurality of slots are open-ended on the distal most end of the inflow cannula.

In another aspect of this embodiment, the rotor is an impeller configured to impel fluid along the major longitudinal axis.

In another aspect of this embodiment, the rotor is an impeller configured to impel fluid perpendicular to the major longitudinal axis.

In another aspect of this embodiment, each of the plurality of slots has a cross-sectional area which increases in an inward direction from the exterior of the inflow cannula.

In another aspect of this embodiment, the inflow cannula defines a lumen there through, and wherein total cross-sectional area of the plurality of slots is greater than a cross-sectional area of the lumen.

In another aspect of this embodiment, each of the plurality of slots defines a width transverse to the inward direction and the width of each of the plurality of slots increases toward the upstream end.

In another aspect of this embodiment, the plurality of slots are equally spaced about the distal end of the inflow cannula.

In another aspect of this embodiment, the inflow cannula is sized to be implanted within a heart of a patient.

In another aspect of this embodiment, the aspect ratio of each of the plurality of slots is between 1:1 and 2:1.

In another embodiment, a blood pump includes a housing defining a fluid flow path. The housing defines an upstream end, a downstream end, and an outlet at the downstream end. A rotor is disposed within the housing and within the fluid flow path. The rotor is rotatable independent of the housing in a first direction and configured to pump blood downstream toward the outlet. The housing defines an inflow cannula at the upstream end, the inflow cannula defining a lumen there through in fluid communication with the outlet end and defining a cross-sectional area. The inflow cannula defines a proximal end proximate the rotor and an opposite distal end, the distal end of inflow cannula defining a plurality of open-ended slots radially disposed about the distal end, the plurality of open-ended slots being angled in the first direction and defining a cross-sectional area greater than the cross-sectional area of the lumen.

In another aspect of this embodiment, a stator is disposed within the housing and has a plurality of electromagnetic coils, the stator is configured to generate an electromagnetic field to rotate the rotor.

In another aspect of this embodiment, the rotor defines a plurality of fluid flow slots, and wherein the number of slots in the plurality of fluid flow slots is different than the number of slots in the plurality of slots.

In another aspect of this embodiment, the rotor is an impeller configured to impel fluid along the major longitudinal axis.

In another aspect of this embodiment, rotor is an impeller configured to impel fluid perpendicular to the major longitudinal axis.

In another aspect of this embodiment, each of the plurality of slots has a cross-sectional area which increases in an inward direction from the exterior of the inflow cannula.

In another aspect of this embodiment, a total cross-sectional area of the plurality of slots is greater than a cross-sectional area of the lumen.

In yet another embodiment, a blood pump includes a housing defining a fluid flow path. The housing defines an upstream end, a downstream end, and an outlet at the downstream end. A rotor is disposed within the housing and within the fluid flow path, the rotor is rotatable independent of the housing in a first direction and configured to pump blood downstream toward the outlet. The housing defines an inflow cannula at the upstream end, the inflow cannula defines a lumen there through in fluid communication with the outlet end and defining a cross-sectional area. The inflow cannula defining a proximal end proximate the rotor and an opposite distal end, the distal end of inflow cannula defining a plurality of open-ended slots radially disposed about the distal end, the plurality of slots being sloped in the first direction with respect to the major longitudinal axis; angled in the first direction with respect to the minor longitudinal axis; and defining a total cross-sectional area greater than a cross-sectional area of the lumen. The rotor defines a plurality of fluid flow slots, and wherein the number of slots in the plurality of fluid flow slots is different than the number of slots in the plurality of slots.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
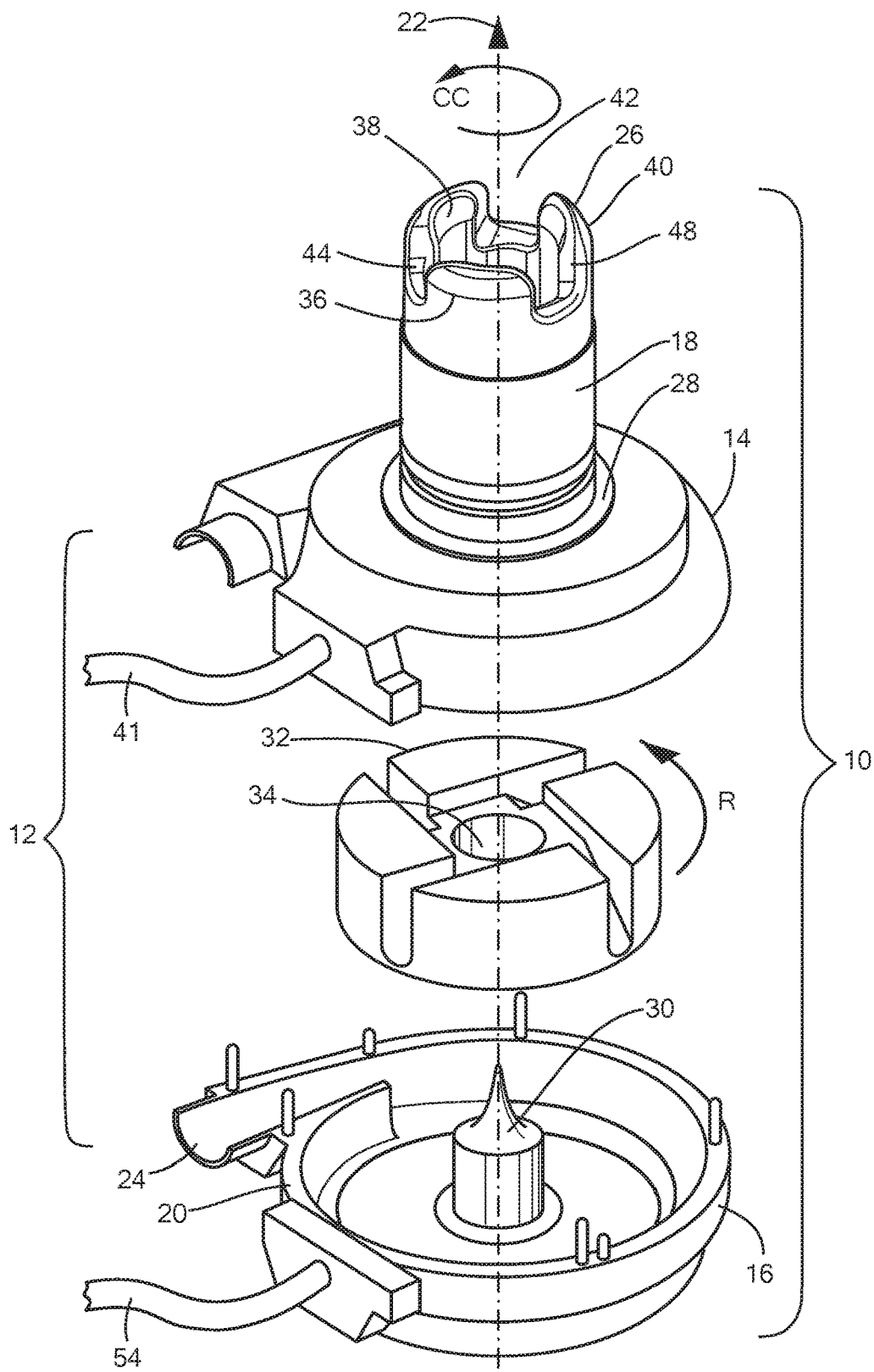
FIG. 1 is a diagrammatic, exploded, perspective view of a blood pump according to one embodiment of the disclosure.

Referring now to the drawings in which like reference designators refer to like elements there is shown in FIG. 1 an exemplary blood pump constructed in accordance with the principles of the present application and designated generally "10. The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18. The first portion 14 and the second portion 16 cooperatively define a volute-shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

Figure 2:
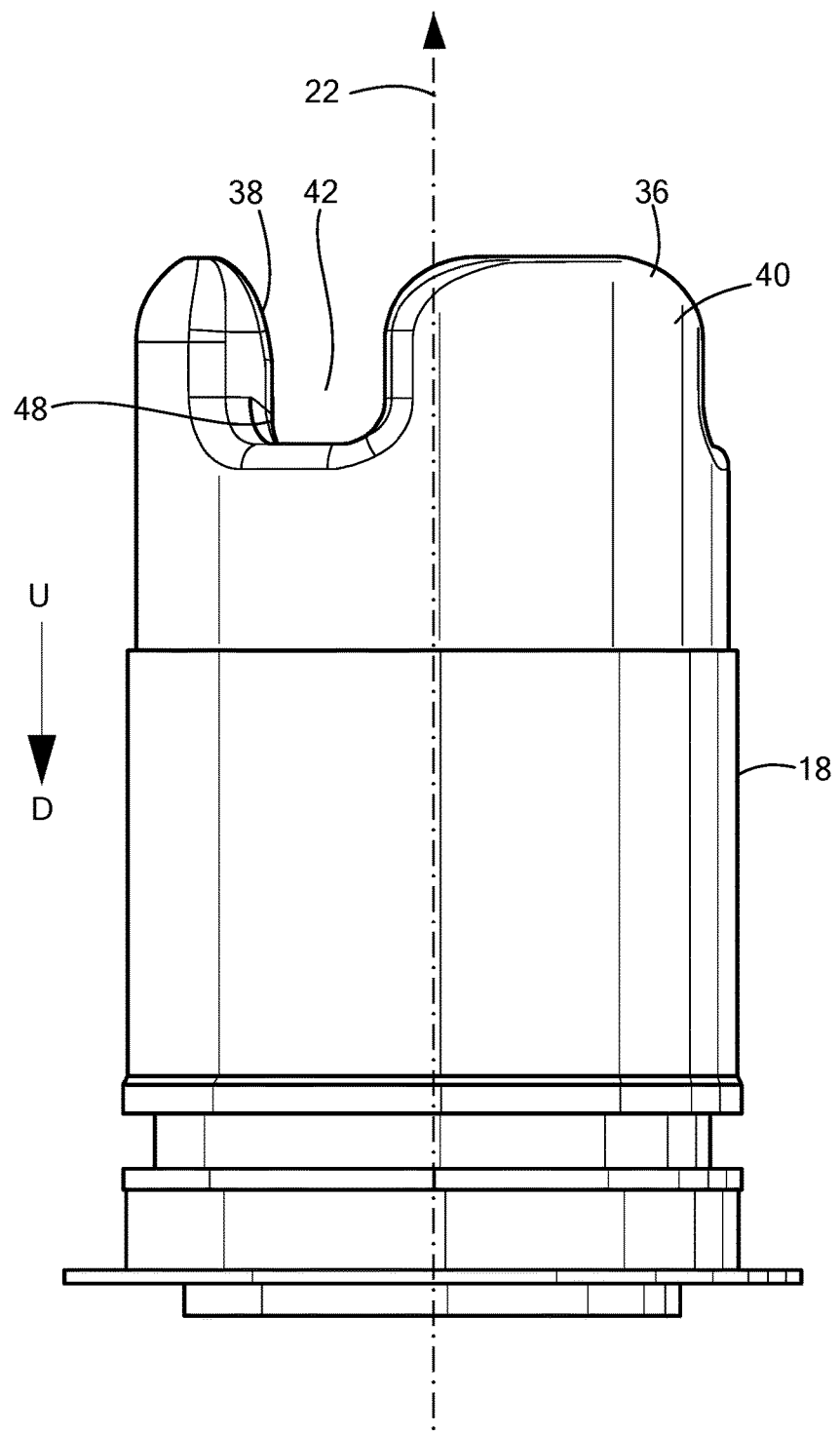
FIG. 2 is a front view of the cannula shown in FIG. 1.
Figure 3:
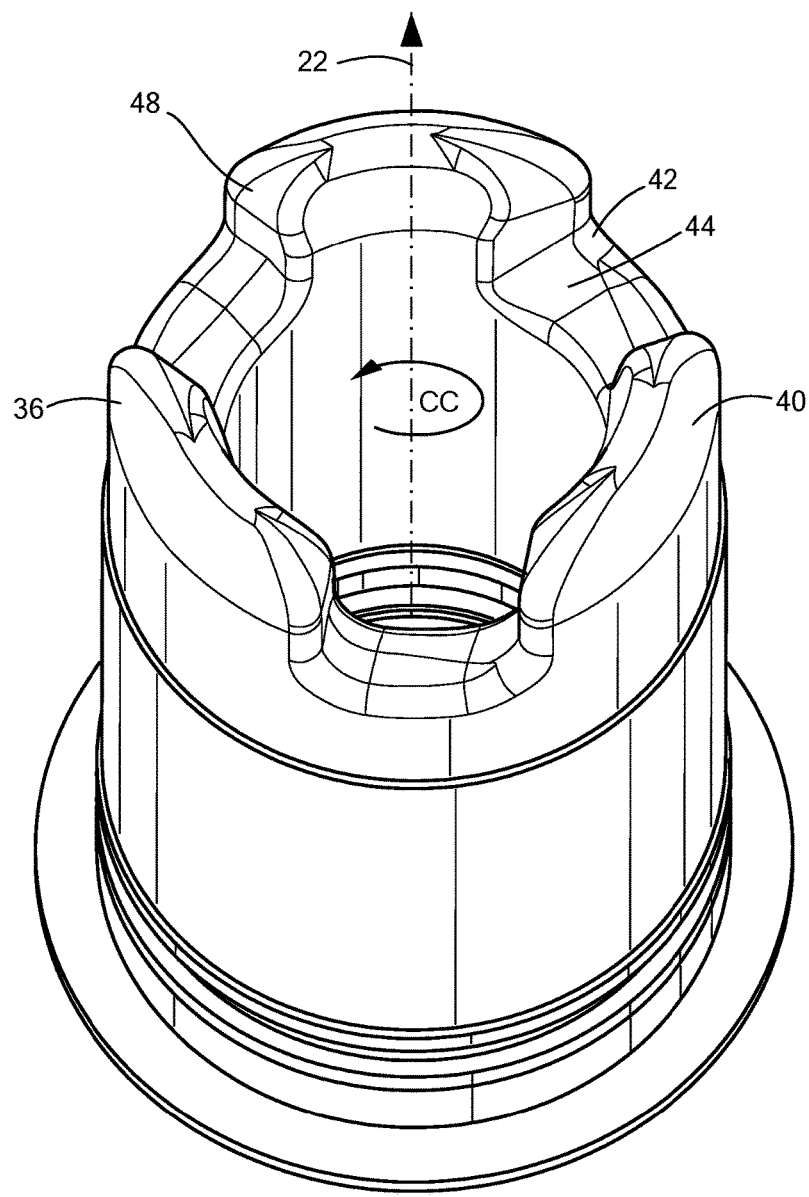
FIG. 3 is a top perspective view of the cannula shown in FIG. 2.

Referring now to FIGS. 1, and 2, the inflow cannula 18 is generally cylindrical and extends from first portion 14 and extends generally along axis 22. The inflow cannula 18 has to an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 (best seen in FIG. 2) at the upstream end of the flow path to the outlet 24 at the downstream end of the flow path. The upstream and downstream directions along the flow path are indicated in FIG. 2 by the arrows U and D respectively. A post 30 is mounted to first portion 14 along axis 22. A generally disc-shaped ferromagnetic rotor 32 with a central hole 34 is mounted within chamber 20 for rotation about the axis 22. Rotor 32 includes a permanent magnet and also includes flow channels for transferring blood from adjacent the center of the rotor to the periphery of the rotor. In the assembled condition, post 30 is received in the central hole of the rotor 32. Components such as permanent magnets electromagnetic coils may be disposed within the first portion 14 and the second portion 16 and in fluidly isolated chambers An electrical connector 41 (FIG. 1) is provided on first portion 14 for connecting the coils to a source of power such as a controller (not shown). The controller is arranged to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise, that is the rotor 32 rotates in a clockwise direction and the slots 42 are angled and/or sloped in the clockwise direction. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with the surfaces of the elements of the first portion 14 and the second portion 16 during operation. The general arrangement of the components described above may be similar to the blood pump 10 used in the MCSD sold under the designation HVAD by Heartware, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Figure 4:
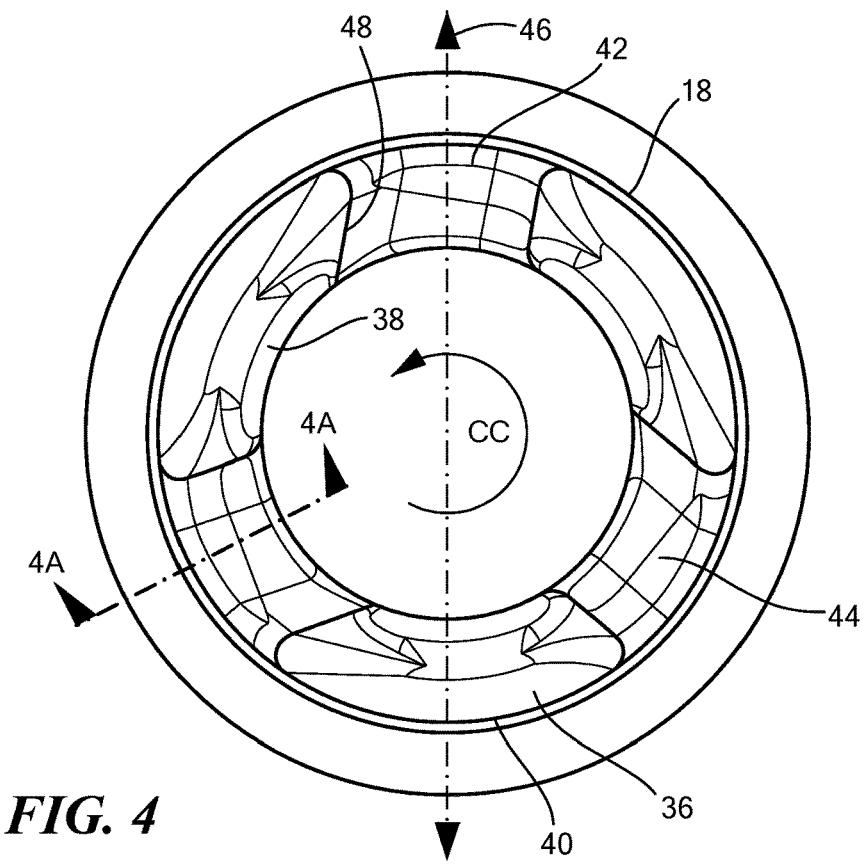
FIG. 4 is a top view of the cannula shown in FIG. 2.
Figure 4A:
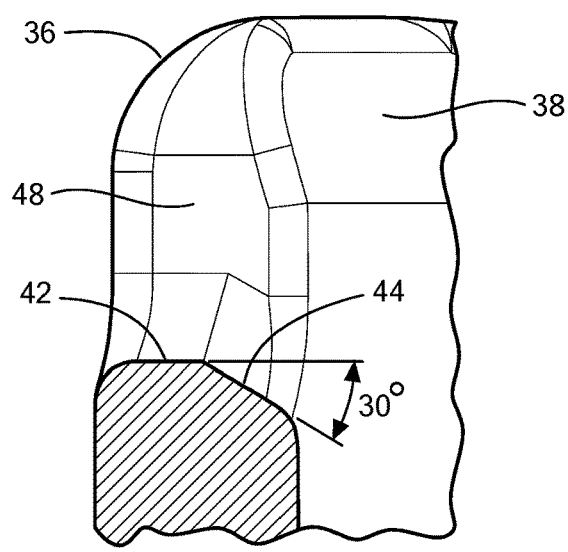
FIG. 4A is a cross-sectional view across Section 4A-4A shown in FIG. 4.

Continuing to refer to FIGS. 1 and 2, the inflow cannula 18 defines a plurality of projections 36 extending in the upstream direction at the upstream end 26. Although three projections 36 are shown, any number of projections 36 may be included. In one configuration, the projections 36 are spaced at equal intervals around the upstream-to-downstream axis 22 and in other configurations, the projections 36 are unevenly spaced. Each projection 36 has an interior surface 38 facing generally in a radially inward direction toward axis 22 and an exterior surface 40 facing generally radially outwardly. The exterior surfaces 40 of the projections 36 constitute an exterior surface of the inflow cannula 18. Projections 36 are spaced apart from one another so as to define corresponding slots 42 disposed between a pair of projections 36, defining a crenellated configuration. The slots 42 may extend generally inwardly from the exterior surface 40 of the inflow cannula to the lumen of the inflow cannula 18. Any number of slots 42 may be included and in one configuration, the number of slots 42 is different than the number of fluid channels in the rotor 32, whether greater or less than. For example, as shown in FIG. 1, the rotor 32 defines four fluid channels and inflow cannula defines three slots 42. Each slot 42 is in the form of a groove that is open at the upstream extremity of the inflow cannula 18, i.e., the slots 42 are bounded on three sides by the inflow cannula 18 but are open at the most distal end of the inflow cannula 18. As best appreciated with reference to FIG. 4, each slot 42 slopes downstream in a circumferential direction CC around axis 22. As further discussed below, the slope of the slots 42 imparts a swirl to blood entering the lumen of the inflow cannula 18 in the circumferential direction C. As depicted in FIGS. 1-4, the circumferential direction CC is counterclockwise around axis 22 as seen in FIG. 4, looking in the downstream direction along axis 22. The circumferential direction CC is the same as the rotational direction R (FIG. 1) of the rotor 32. Each slot 42 has a floor or proximal surface 44 (FIGS. 3, 4, 4A) facing generally in the downstream direction and forming the downstream wall of the slot 42. As best appreciated with reference to FIG. 4A, a floor surface 44 of each slot 42 has a sufficient thickness to enable to the floor surface 44 to slope in the downstream direction D from a point along the slot 42 proximate the exterior surface 40 to the juncture between the slot 42 and the interior wall of the inflow cannula 18. For example, FIG. 4A illustrates a 30 degree slope in the floor surface 44 in the downstream direction, although slopes in the range from greater than 0 degrees to 90 degrees are contemplated. Thus, the cross-sectional area of each slot 42 increases progressively in the inward direction, toward axis 22. The floor surface 44 of each slot 42 also in angled in downstream in the circumferential direction CC. That is, the inflow cannula 18 defines the axis 22 and minor longitudinal axis 46 perpendicular to the axis 22. Each of the plurality of slots may be sloped in the first direction CC with respect to the axis 22 and/or angled in the first direction CC with respect to the minor longitudinal axis 46. Each slot 42 also has side surfaces 48 defined by edges of the slots 42, extending upstream from floor surface 44 and bounding the slots 42 on circumferentially opposite sides. These side surfaces 48 extend generally upstream and downstream, but flare outwardly, away from one another adjacent the upstream extremities of the slots and slots. The surfaces of the slots 42, and the slots 42 generally, are rounded and smooth at the exterior surface 40 of the inflow cannula 18 and at the upstream extremities of the slots 42. In other configurations, the rotor 32 rotates in a clockwise direction. For example, the rotor 32 may be configure to impel blood in a direction parallel to the axis 22 as opposed to perpendicular to axis 22. In such a configuration, each of the slots 42 may be angled and sloped, as described above, in the clockwise direction. The slots 42 may further be of uniform size or alternatively may vary in size. In one configuration, the aspect ratio of each of the slots 42 is between 1:1 and 2:1, and in an exemplary configuration, 1.22:1.

In one configuration, the surface area of the slots 42 is equal to or greater than the surface area defined by the interior flow of the inflow cannula 18. That is the sum of all the surface areas of each slot 42, independent of the number of slots 42, is greater than the cross-sectional area of the lumen of the inflow cannula 18. This configuration, combined with the slots 42 being angled and sloped in the direction of rotation CC of the rotor may result in increased washing efficiency around the exterior surface 40 of the inflow cannula 18 when in implanted within the heart, by around 25%, as compared to an un-crenellated design, which further prevents the formation of thrombus. For example, in one configuration, the washing efficiency increases around the exterior surface 40 of the inflow cannula 18 linearly for about 300 microns radially outward from the inflow cannula 18, when the pump is implanted within the left ventricle.

Figure 5:
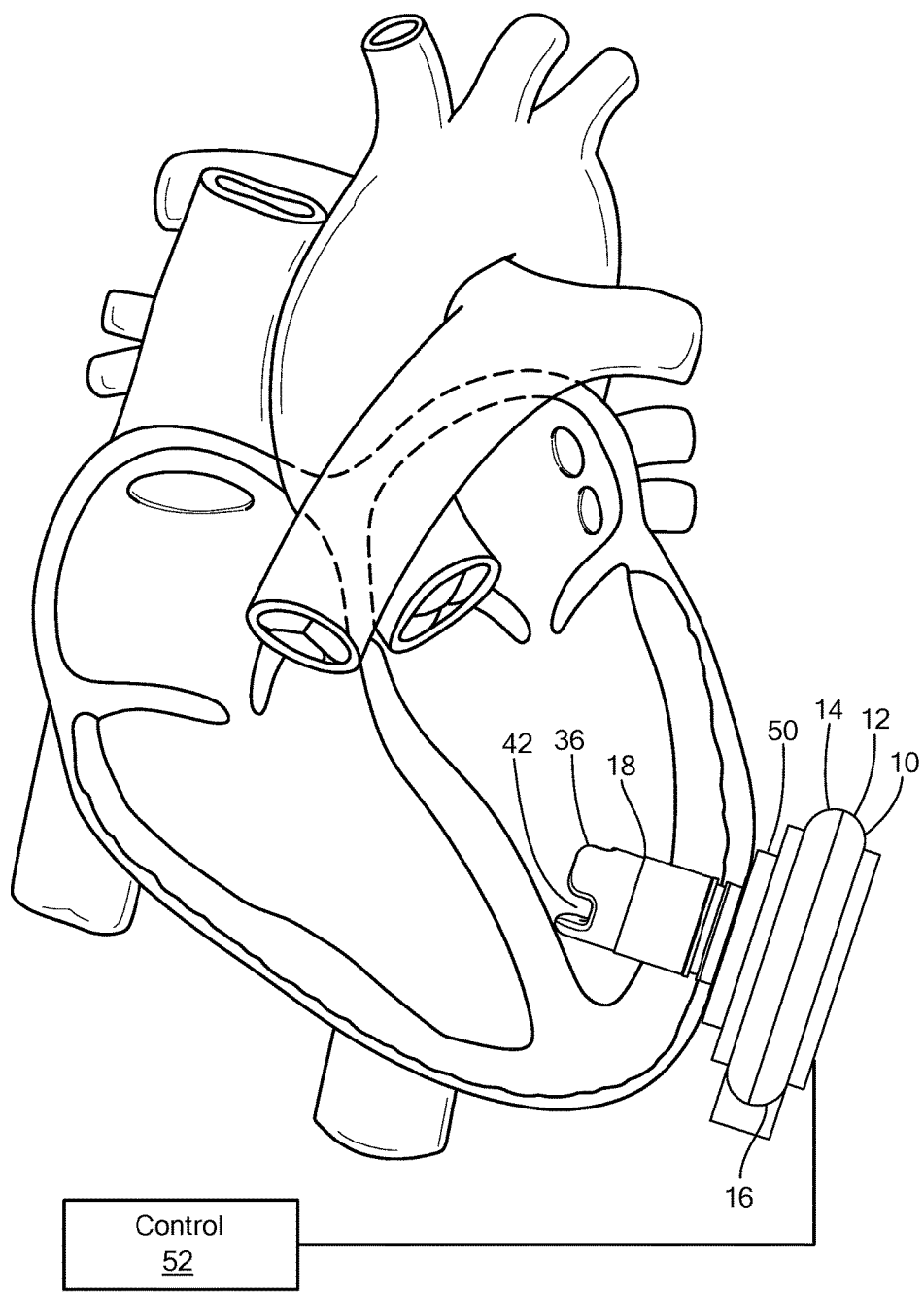
FIG. 5 is a diagrammatic view depicting a heart with the pump of FIG. 1 implanted therein.

In a method according to a further aspect of the disclosure, pump 10 is implanted in a mammalian subject, such as a human patient, so that the upstream end 26 of inflow cannula 18 projects into a chamber of the heart, such as the left ventricle (LV), as depicted schematically in FIG. 5. For example, a mounting ring such as a mounting ring 50 may be attached to an exterior surface of the heart wall as, for example, by suturing it to the heart wall adjacent the apex of the heart. A hole may be formed through the heart wall within the mounting ring. The inflow cannula 18 is advanced through the mounting ring and through the hole in the heart wall, and a clamp (not shown) incorporated in the mounting ring 50 is actuated so that the mounting ring grips the outlet structure, thus attaching the pump to the mounting ring and to the heart. In an exemplary configuration, the first portion 14 and the second portion 16 are disposed outside of the heart. An outlet cannula such as a flexible tubular outlet cannula (not shown) is connected between the outlet 24 and an artery such as the aorta. Pump 10 is operatively connected to a controller 52, as, for example, by electrically connecting the controller to the pump via connector 54 (FIG. 1) so that the controller can actuate the pump and control its operation. Controller 52 may be mounted within or outside of the patient's body.

With the pump mounted in place on the heart, electric power is supplied to the electromagnetic coils of the pump by controller 52. The rotor 32 (FIG. 1) rotates about the central axis 22 at a speed set by the controller, so that the pump 10 draws blood from within the ventricle LV and transfers it to the aorta. Typically, the controller adjusts the electric power supplied to the pump 10 so as to maintain the rotor speed and hence the average blood flow through the pump 10 at a value less than the entire flow of blood entering the left ventricle over time. That is, the heart itself performs some of the pumping action necessary to pump blood into the aorta against the prevailing arterial blood pressure. In this normal condition, the pressure prevailing within the left ventricle is at least slightly above the pressure prevailing around the outside of the heart throughout the cardiac cycle.

Figure 6:
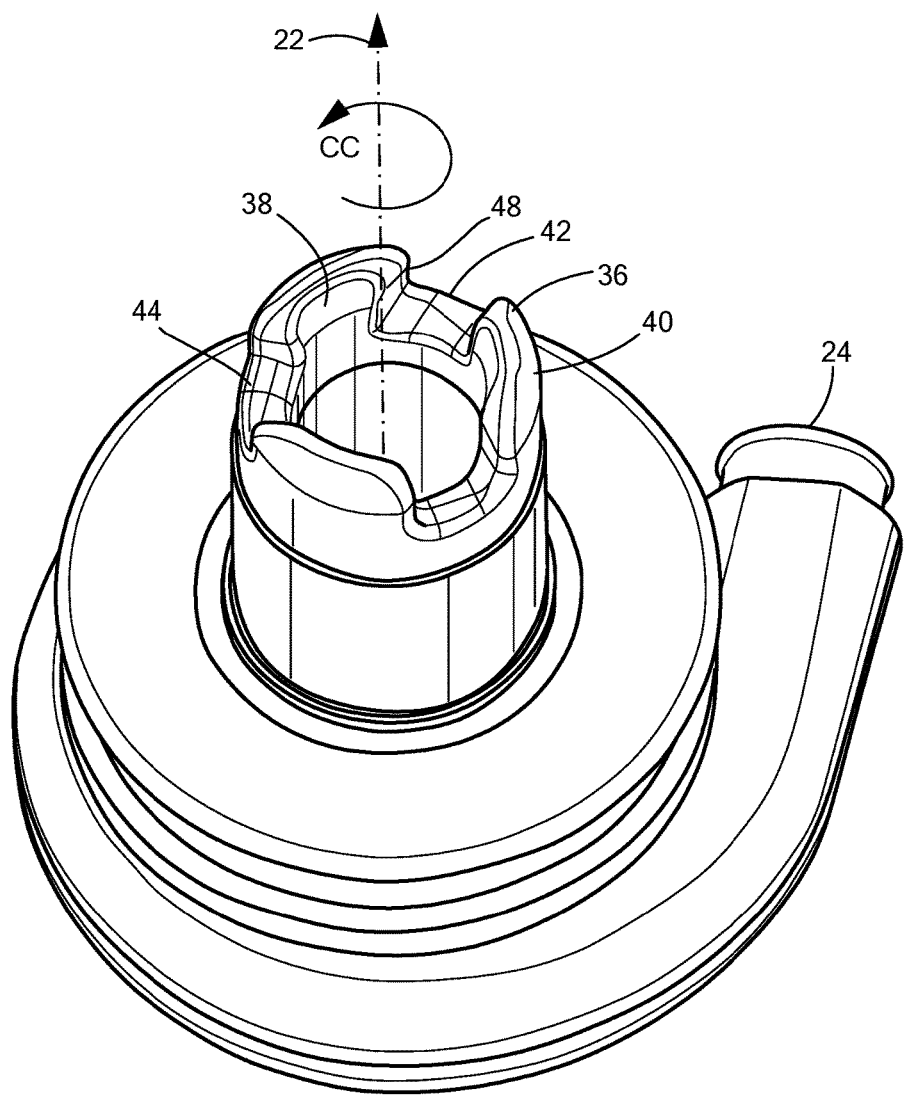
FIG. 6 is an assembled view of the blood pump shown in FIG. 1.

In this normal operating condition, the pump draws in blood through the inflow cannula 18. Typically, a substantial portion of the blood entering the inflow cannula passes in the downstream direction through upstream end 26 and passes through the flow path of the pump to the outlet. The blood flowing through the slots 42 imparts angular momentum or swirl about axis 22 to the flow as a whole. As discussed above, in this embodiment, the actual direction of swirl is the counter-clockwise direction CC shown in FIG. 6, co-directional with the counter0clockwise rotation of the rotor. This swirl improves the hydrodynamic efficiency of the pump 10. In other embodiments, with a different rotor configuration, swirl counter-directional to the rotational direction of the rotor can provide improved hydrodynamic efficiency. During normal operation, the walls bounding the heart chamber, such as the interventricular septum IVS and the outside wall of the wall VW bounding left ventricle LV, remain remote from the upstream end 26 of the inflow cannula 18. Changes in the patient's physiology as, for example, changes in the prevailing arterial pressure, the patient's state of activity, or other changes in the body, may decrease the average rate of flow into the left ventricle, increase the rate of flow from the left ventricle to the aorta, or both. In this condition, the ventricle in continually drained of blood. This may cause the walls bounding the ventricle to collapse towards one another. This is referred to as a suction condition. In the suction condition, one or more of the walls may overlie the upstream end 26 of the inflow cannula 18 and thus fully or partially close the inflow cannula 18. However, blood will continue to flow into the pump through slots 42. While one or more of the slots 42 may be blocked in this condition, it is unlikely for the walls to collapse in such a manner as to block all of the slots and the upstream opening simultaneously. Thus, even in a suction condition, the inlet to the pump will remain at least partially open.

Continued operation of the pump may not cause an extreme drop in the pressure prevailing at the inlet to the flow path, just downstream of any partial blockage. This limits the differential pressure applied to the heart wall causing the blockage and thus limits the force tending to engage the heart wall with the inflow cannula. This, in turn, minimizes damage to the tissue of the heart wall that could be caused by forcible engagement with the inflow cannula. Moreover, limiting the force of engagement between the heart wall and the inflow cannula 18 in the event of a suction condition makes it easier to detach the heart wall from the inflow cannula 18 when the suction condition is cleared and the blood reinflates the ventricle. The outward splay of the side surface 28 of the slots 42 and the gentle, rounded curves of the surfaces at the upstream extremity of the inflow cannula 18 also makes it easier to detach the heart wall from the inflow cannula when the suction condition is relieved.

The controller 52 associated with the pump 10 is configured to detect a suction condition and to vary the operation of the pump 10 so as to relieve the suction condition. For example, controller 52 may detect changes in flow through the pump, power consumption by the pump, pressure prevailing within the pump 10 or within the chamber, flow rate through the pump 10 or other operational parameters. The controller 52 may be configured to temporarily reduce the operating speed of the pump in response to a suction condition. Suction detection and correction may be performed, for example, by a controller as taught in U.S. Published Patent Application No. 2015/0367048, the disclosure of which is hereby incorporated by reference herein. Stated another way, the suction-detecting controller and the inflow cannula 18 cooperate to provide effective relief of suction conditions.

Numerous variations and combinations of the features discussed above can be utilized. For example, the number of slots and slots can be varied. The inflow cannula 18 can be applied to other pumps. For example, an inflow cannula 18 as described herein can be provided on an axial flow blood pump. Certain axial flow blood pumps are described in U.S. Pat. No. 8,007,254, the disclosure of which is hereby incorporated by reference herein and a copy of which is annexed hereto as a part of this disclosure, have a generally straight, tubular housing, so that one end of the tubular structure forms the inflow cannula 18 whereas the other end forms the outlet. The impeller is arranged to rotate around the axis of the housing and to impel blood in a downstream direction through the flow path defined by the structure. Here again, the inflow cannula 18 may be modified to include slots and slots as described herein. In some cases, axial flow blood pumps are positioned with the inflow cannula inside a heart chamber such as the ventricle and with the outlet end of the pump outside of the heart, so that the outlet structure is connected to an artery such as the aorta via a flexible inlet cannula in much the same manner as described above with reference to FIG. 5. In other cases, axial flow blood pumps of this nature can be mounted with the entire housing of the pump disposed within the ventricle. For example, as shown in U.S. Pat. No. 8,852,072, the disclosure of which is also incorporated herein by reference, an axial flow blood pump may be mounted inside the heart chamber and retained in place by a rigid elongated member extending from the inlet end of the pump to a fixation device mounted on the heart wall. The outlet of the pump typically is connected to an outlet cannula that extends out of the ventricle into the aorta through the aortic valve of the heart. Here again, the inlet of the pump may be provided with slots and slots as discussed herein.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A blood pump, comprising:
   a housing defining a fluid flow path, the housing defining an upstream end, a downstream end, and an outlet at the downstream end;
   a rotor disposed within the housing and within the fluid flow path, the rotor being rotatable independent of the housing in a first direction and configured to pump blood downstream toward the outlet; and
   the housing defining an inflow cannula at the upstream end, the inflow cannula defining a lumen there through in fluid communication with the outlet end and defining a cross-sectional area, the inflow cannula defining a proximal end proximate the rotor and an opposite distal end, the distal end of inflow cannula defining a plurality of open-ended slots radially disposed about the distal end, the plurality of open-ended slots define a respective floor surface spanning a thickness of the inflow cannula between an exterior surface of the inflow cannula and an interior surface of the inflow cannula, the floor surface being sloped toward the downstream end and angled in the first direction.

2. The blood pump of claim 1, further including a stator disposed within the housing and having a plurality of electromagnetic coils, the stator being configured to generate an electromagnetic field to rotate the rotor.

3. The blood pump of claim 1, wherein the rotor defines a plurality of fluid flow slots, and wherein the number of slots in the plurality of fluid flow slots is different than the number of slots in the plurality of slots.

4. The blood pump of claim 1, wherein the rotor is an impeller configured to impel fluid along the major longitudinal axis.

5. The blood pump of claim 1, wherein the rotor is an impeller configured to impel fluid perpendicular to the major longitudinal axis.

6. The blood pump of claim 1, wherein each of the plurality of slots has a cross-sectional area which increases in an inward direction from the exterior of the inflow cannula.

7. A blood pump, comprising:
a housing defining a fluid flow path, the housing defining an upstream end, a downstream end, and an outlet at the downstream end;
a rotor disposed within the housing and within the fluid flow path, the rotor being rotatable independent of the housing in a first direction and configured to pump blood downstream toward the outlet; and
the housing defining an inflow cannula at the upstream end, the inflow cannula defining a proximal end proximate the rotor and an opposite distal end, the inflow cannula further defining a major longitudinal axis, minor longitudinal axis, an exterior surface and an interior surface, the distal end of inflow cannula defining a plurality of slots radially disposed about the distal end, each of the plurality of slots being open-ended on the distal most end of the inflow cannula and defines a respective floor surface spanning a distance between the exterior surface and the interior surface, the floor surface including a sloped portion, the sloped portion being sloped toward the downstream end and toward the fluid flow path from a point proximate the exterior surface to a juncture between the respective slot and the interior surface.

8. The blood pump of claim 7, wherein the housing defines a rotor space, and wherein the rotor is disposed within the rotor space, and wherein the inflow cannula is mounted in fixed spatial relationship with the rotor space.

9. The blood pump of claim 7, wherein the rotor defines a plurality of fluid flow slots, and wherein the number of slots in the plurality of fluid flow slots is different than the number of slots in the plurality of slots.

10. The blood pump of claim 7, wherein the rotor is an impeller configured to impel fluid along the major longitudinal axis.

11. The blood pump of claim 7, wherein the rotor is an impeller configured to impel fluid perpendicular to the major longitudinal axis.

12. The blood pump of claim 7, wherein each of the plurality of slots has a cross-sectional area which increases in an inward direction from the exterior of the inflow cannula.

13. The blood pump of claim 12, wherein the inflow cannula defines a lumen there through, and wherein total cross-sectional area of the plurality of slots is greater than a cross-sectional area of the lumen.

14. The blood pump of claim 13, wherein each of the plurality of slots defines a width transverse to the inward direction and the width of each of the plurality of slots increases toward the upstream end.

15. The blood pump of claim 7, wherein the plurality of slots are equally spaced about the distal end of the inflow cannula.

16. The blood pump of claim 7, wherein the inflow cannula is sized to be implanted within a heart of a patient.

17. The blood pump of claim 7, wherein an aspect ratio of each of the plurality of slots is between 1:1 and 2:1.

18. The blood pump of claim 7, wherein the floor surface includes a planar portion adjacent to the sloped portion.

19. A blood pump, comprising:
a housing defining a fluid flow path, the housing defining an upstream end, a downstream end, and an outlet at the downstream end;
a rotor disposed within the housing and within the fluid flow path, the rotor being rotatable independent of the housing in a first direction and configured to pump blood downstream toward the outlet; and
the housing defining an inflow cannula at the upstream end, the inflow cannula defining a lumen there through in fluid communication with the outlet end and defining a cross-sectional area, the inflow cannula defining a proximal end proximate the rotor and an opposite distal end, the distal end of inflow cannula defining a plurality of open-ended slots radially disposed about the distal end, the inflow cannula defining a major longitudinal axis and a minor longitudinal axis, the plurality of slots define a respective floor surface spanning a thickness of the inflow cannula between an exterior surface of the inflow cannula and an interior surface of the inflow cannula, the floor surface being sloped toward the downstream end and angled in the first direction toward the fluid flow path, the plurality of slots further defining a total cross-sectional area greater than a cross-sectional area of the lumen; and
the rotor defines a plurality of fluid flow slots, the number of slots in the plurality of fluid flow slots is different than the number of slots in the plurality of slots.

* * * * *